(12) United States Patent
Canary et al.

(10) Patent No.: US 6,541,645 B1
(45) Date of Patent: Apr. 1, 2003

(54) ELECTRON-DRIVEN CHIRALITY SWITCHES

(75) Inventors: James W. Canary, New York, NY (US); Steffen Zahn, Waltham, MA (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 09/626,167

(22) Filed: Jul. 26, 2000

Related U.S. Application Data

(60) Provisional application No. 60/145,261, filed on Jul. 26, 1999.

(51) Int. Cl.[7] .............................. C07F 1/08; C07F 3/06
(52) U.S. Cl. .......................... 549/5; 549/10; 556/115; 556/116
(58) Field of Search .................................. 556/115, 116; 549/5, 10; 548/101

(56) References Cited

PUBLICATIONS

Anelli, et al., "Molecular Meccano. 1. [2]Rotaxanes and a [2]Catenane Made to Order," *J. Am. Chem. Soc.* 114(1):193–218 (1992).
Zahn, et al., "Electron–Induced Inversion of Helical Chirality in Copper Complexes of N,N–Dialkylmethionines," *Science* 288:1404–1407 (2000).
Zahn, et al., "Absolute Configurations of N,N–Dialkyl α–Amino Acids and β–Amino Alcohols from Exciton––Coupled Circular Dichroism Spectra of Cu(II) Complexes," *Organic Letters* 1(6):861–864 (1999).
Zahn, et al., "Redox–Switched Exciton–Coupled Circular Dichroism: A Novel Strategy for Binary Molecular Switching," *Angew. Chem. Int. Ed.* 37(3):305–307 (1998).
Zellkovich, et al., "Molecular Redox Switches Based on Chemical Triggering of Iron Translocation in Triple–Stranded Helical Complexes," *Letters To Nature* 374:790–792 (1995).
Fernandez–Acebes, et al., "Optical Switching and Fluorescence Modulation in Photochromic Metal Complexes," *Adv. Mater.*, 1998, 1519–1522, 10(18).
Belle, et al., "A Molecular Redox Switch via Iron Translocation ina Biocompartmental Ligand," *NEW J. CHEM.* 22:1399–1402 (1998).
Burk, et al., "New Chiral $C_3$ –Symmetric Tripodal Phosphanes," *ANGEW CHEM INT. ED. ENGL.* 12:1462–1464 (1990).
Canary, et al., "Conformationally Driven, Propeller–like Chirality in Labile Coordination Complexes," *Journal of American Chemical Society* 117:8484–8485 (1995).

(List continued on next page.)

*Primary Examiner*—Porfirio Nazario-Gonzalez
(74) *Attorney, Agent, or Firm*—Browdy and Neimark, P.L.L.C.

(57) ABSTRACT

Complexes of organic ligands with a metal ion exhibit unique conformation and spectroscopic properties upon changes in oxidation state of the metal ion. The metal is a redox-active metal ion and may possess additional ligands bonded to it. The organic ligand has three "arms" that are linked together at a central atom; each arm contains atoms that may also coordinate to the metal ion. At least two of the arms possess chromophoric properties. At least one arm contains two different groups that may coordinate to the metal ion. In one oxidation state, a first atom binds to the metal. In a second oxidation state, a second atom binds to the metal. This change in coordination of the metal ion results in a rotation of one of the arms, which changes the orientation of another group, which inverses the orientation of the two chromophoric species with respect to one another.

11 Claims, 9 Drawing Sheets

OTHER PUBLICATIONS

Canary et al., "Solid State and Solution Characterization of Chiral, Conformationally Mobile Tripodal Ligands," *INORGANIC CHEMISTRY* 37(24):6255–6262 (1998).

Castagnetto, et al., "Absolute Configurational Assignment of Self–Organizing Assymmetric Tripodal Ligand Complexes," *Chirality*, 9:616–622 (1997).

Castagnetto, et al., "A Chiroptically Enahanced Fluorescent Chemosensor," *CHEM.COMMUN.* 4:203–204 (1998).

Canevet, et al., "Molecular Redox–Switches by Ligand Exchange," *ANGEW. CHEM. INT. ENGL.* 35(22):2657–2660 (1996).

Feringa, et al., "Chiroptical Molecular Switch," *J. AM. CHEM. SOC.*, 113:5468–5470 (1991).

Kawai, et al., "A Dual–Mode Molecular Switching Device: Biphenolic Diarylethenes with integrated Photochromic and Electrochromic Properties," *CEHM. EUR. J.* 1(5):285–293 (1995).

Goulle, et al., "An Electro–photoswitch of the Luminescence of a Bipyridine Metal Complex," *J. CHEM. SOC. ,CHEM. COMMUN*, 1034–1036 (1993).

Huck, et al., "Dynamic Control and Amplification of Molecular Chirality by Circular Polarized Light," *SCIENCE* 273:1686–1688 (1996).

Janicki, et al., "A Liquid Crystal Opto–optical Switch: Nondestructive Information Retrieval Based on a Photochromic Fulgide as Trigger," *J. AM. CHEM. SOC.* 117:8524–8527 (1995).

Livoreil, et al., "Electrochemically Triggered Swinging of a [2]–Cetenate," *J. AM. CHEM. SOC.* 117:8524–8527 (1995).

Livoreil, et al., "Electrochemically Triggered Swinging of a [2]–Cetanate," *J. AM. CHEM. SOC.* 116:9399–9400 (1994).

Otsuki, et al., "Supramolecular Electro–and –Proto–Photoswitch," *CHEMISTRY LETTERS* 269–270 (1999).

Spreitzer, et al., "Multi–Mode Switching Based on Dihydroazulene/Vinylheptafulvene Photochromism: Synergism of Photochromism and Redox Switching in Heteroaryl––Functionalized Systems," *CHEM. EUR. J.* 2(9):1150–1158 (1996).

Chunag, et al., "Synthesis, Cyclic Voltammetry, and X–ray Crystal Structures of Copper(I) and Copper(II) Complexes of Tris((6–phenyl–2–pyridyl)methyl)amine (TPPA)," *INORGANIC CHEMISTRY* 34:2562–2568 (1995).

Fabbrizzi, et al., "Sensors and Switches from Supramolecular Chemistry," *CHEMICAL SOCIETY REVIEWS* 197–202 (1995).

Anelli, et al., "Molecular Meccano. 1. [2]Rotaxanes and a [2]Catenane Made to Order," *J. AM. CHEM. SOC.* 114(1):193–218 (1992).

Zahn, et al., "Electron–Induced Inversion of Helical Chirality in Copper Complexes of N, N–Dialkylmethionines," *SCIENCE* 288:1404–1407 (2000).

Zahn, et al., "Absolute Configurations of N,N–Dialkyl β–Amino Acids Alcohols from Exciton–Coupled Circular Dichroism Spectra of Cu(II) Complexes," *ORGANIC LETTERS* 1(6):861–864 (1999).

Zahn, et al., "Redox–Switched Exciton–Coupled Circular Dicroism: A Novel Strategy for Binary Molecular Switching," *ANGEW. CHEM. INT. ED.* 37(3):305–307 (1998).

Zellkovich, et al., "Molecular Redox Switches Based on Chemical Triggering of Iron Translocation in Triple–Stranded Helical Complexes," *LETTERS TO NATURE* 374:790–792 (1995).

DHA  ⇌  VHF 1        2

5 (R=Et, α-EtBQPA)
6 (R=CH Ph, α-BnBQPA)
7 (R=i-Pr, α-i-PrBQPA)
8 (R=Ph, α-PhBQPA)

ELECTRON-DRIVEN CHIRALITY SWITCHES

CROSS-REFERENCE TO RELATED APPLICATIONS

This application claims the benefit under 35 U.S.C. §119(e) of U.S. Provisional Application No. 60/145,261, filed Jul. 26, 1999.

This invention was partially supported by NIH grant GM49170 and ACS-PRF grant 33491-ACS.

FIELD OF THE INVENTION

The present invention is directed to three dimensional metal ion complexes containing chromophores that can be manipulated by valence changes to result in a change in differential absorption of light.

BACKGROUND OF THE INVENTION

Chiral coordination complexes are frequently used in asymmetric synthesis and chiral discrimination technologies (Eliel et al., 1994). Recently, $C_3$-symmetric chiral ligands have shown great potential for enantioselective reactions, yet few such compounds are available (Burk et al., 1990).

A recent and exciting prospect in the area of information technology lies in the development of molecular switches that operate with efficiency, reversibility, and resistance to fatigue (Lehn, 1995). The development of electrochemical switches has recently attached much attention due to applications such as data storage (Huck et al., 1996).

Redox switches require:
  (A) components whose structures and physical properties can be turned on or off electrochemically (Fabbrizzi et al., 1995); and
  (B) sufficiently different optical spectra that allow the individual states to be addressed (Huck et al.).

(Feringa et al., 1991) have used isomerism in thioxanthenes to obtain chiroptical switches. Lights of different wavelengths was used to switch between M and P isomers. The difference in chirality/helicity leads to a different response in the circular dichroism (CD), where $\Delta\epsilon\Delta=45(M)$ vs $\Delta\epsilon=49(P)$). The enantiomers 1 and 2 in FIG. 1 were found to be stable at room temperature. Thermal racemization of isomer 1a showed first-order reaction kinetics with a barrier to racemization of 26.4 kcal/mol. Cis-trans isomerization was not observed under ambient conditions. On the other hand, irradiation of pure 1a, presumably at ambient temperature, yielded 64% 1a and 36% 2a, with no observable racemization, while irradiation at 250 nm gave 68% 1a and 32% 2a. Furthermore, alternate irradiation of 1a at 250 and 300 nm caused a modulation of the circular dichroism (CD) signal for 1a at 232 and 262 nm for a switching time of three seconds. Similar behavior was observed for switching times of 0.5 to 60 seconds. Compound 1 could be cycled between cis and trans forms a minimum of 10 times without racemization of changes in the UV and CD spectra. Feringa added his racemate mix to a nematic liquid crystal and then irradiated them with circularly polarized light. The resulting excess of one enantiomer was enough to switch the liquid crystal into its chiral cholesteric phase.

Shining ordinary light on the mix will convert the liquid crystal and the racemate back again (Feringa et al., op. cit.). Important problems that remain to be solved are improved thermal stability, increased fatigue resistance, and structural modification to achieve switching with visible light.

A different approach towards an optical switch was published by Schuster et al. Schuster recognized that in an opto-optical switch, where the position of the switch is transposed with light and sensed with light by change in its absorption spectrum, a fundamental problem is the destructive readout. That is, reading the position of the switch ultimately erases it. To overcome this potential problem, Schuster developed a system consisting of a photochromic fulgide dissolved in a photochemically inert cholesteric liquid crystal that is bistable and switchable by repetitive application of ultraviolet and visible light. In the course of the experiment, he showed that the pitch of a cholesteric liquid crystal can be controlled photochemically by the photochromic fulgide dopant. The pitch changes were measurable at reasonable fulgide concentrations, and both states of the liquid crystal/fulgide mixture are thermally stable under the conditions tested. The change of the pitch was bi-directional and reversible, and is controlled with light of suitable wavelength. According to Schuster, the pitch of the liquid crystal can be read optically without affecting the record information (Janicki et al., 1995). This is shown in FIG. 2. Daub et al. reported a dihydroazulene/vinylheptafulvene photochroism system in which the information is stored and read with light. Besides the disadvantage of both storing and reading with light, the system possesses several chemical modification sites that might permit the tuning and optimization of the switching behavior (Spreitzer et al., 1996). This system is shown in FIG. 3.

Coordination complexes featuring iron in its two distinct oxidation states embedded in a triple stranded ligand were inter-converted by chemical means. This system took advantage of a "hard" binding cavity and a "soft" binding cavity present within the system. The iron literally translocated within the strand depending upon its oxidation state. The process was monitored by the UV (d-d transitions of the Fe(II) as well as the Fe(III) species). The system did not display reversible behavior. In fact, oxidation of the Fe(II) species had to be facilitated at 50° C. in order to obtain the Fe(III) complex (Zelikovich et al., 1995).

Another version of this redox switch inter-converts between two distinct states by ligand exchange. At the heart of this switch is a molecule that possesses two sets of binding groups: one set of hard and one set of soft ligating groups. The two sets are anchored on a calix[4]arene ring in an alternating fashion, such that they can form either a hard or a soft ion biding cavity. One cavity is formed at the exclusion of the other, according to the authors. When loaded with Fe(III), the hard binding groups, hydroxamates, converge to embrace the hard metal ion, while soft groups diverge. Upon reduction, the ligand rearranges to engulf Fe(II) with its soft bipyridyl groups, while the hard groups diverge. Subsequent oxidation reversed the process. This switch action was again followed by UV (Canavet et al., 1996). Stoddart et al. developed a synthetic methodology based on the idea of assembling carefully designed small molecular components in a template-directed manner. The molecular subunits are not held together by classical covalent bonds, but rather by twinning and interlocking, the mechanical interactions responsible for the presence of catenanes, rotaxanes, and knots. They described a synthesis of catenanes and a rotaxane which were able to function as "molecular trains" and a "molecular shuttle." As seen in FIG. 6, the [2]-rotaxane 1, which can operate as a molecular shuttle, consists of a molecular assembly in which a tetracationic bis-pyridinium cyclophane moves back and forth like a shuttle (1<-->2) between two "stations" which are situated symmetrically in a polyether terminated at the ends by large groups that acct as "stoppers." The positively charged cyclophane ring will be attracted equally by the two identical electron-rich hydroquinol groups and therefore jump back and forth between the two stations. Temperature dependent H-NMR spectra indicated that this process occurred 500 times a second (Stoddart et al., 1992).

Lehn et al. reported a molecular switching device 1→2 shown in FIG. 7 that effects the redox on/off switching of luminescence and combines an electroactive component with a light-emitting center. Both the oxidized and reduced forms are isolatable and stable. The reduced form 2 is luminescent, whereas the oxidized form 1 is quenched. The electrochemical interconversion of the two species was reported to be reversible (Goulle et al., 1993).

Another approach by Lehn et al. featured 1,2-diarylethenes that can undergo reversible ring closure. The open form can be converted almost quantitatively into a closed form by UV light at 365 nm. The reverse process can be effected thermally or photochemically, at 600 nm, as shown in FIG. 8. The process was followed by UV (Giltam et al., 1995).

Sauvage et al. reported electrochemically triggered swinging of a [2]-catenate, taking advantage of the principle of bi-stability, as many systems have before. This is shown in FIG. 9. A transition metal complex has an organic backbone consisting of two interlocking rings. One ring contains two binding site, a bi- and a tridentate, whereas the second ring features only one bidentate coordination site. Thus, by interlocking both rings, a tetradentate and a pentadentate ligation site is formed. Introducing Cu(II) into the system leads to the formation of the pentacoordinate complex, whereas Cu(I) will generate the tetra-coordinate species. The interconversion between both forms of the complex is electrochemically triggered and corresponds to the sliding motion of one ring within the other. The process was followed by UV (Livoreil et al., 1994).

Systems that substantially profit from transition metals in terms of fluorescence behavior have been thoroughly investigated by Fabbrizzi et al. In general, this system consists of a redox-active metal, i.e., Cu, Ni, which is positioned within a tetradentate ligand, which is tethered to a fluorophore. Depending on the metal oxidation state, the ET mechanism is active or quenched (Farrbizzi et al., 1995). This system is shown in FIG. 10.

Recently, systems based on ruthenium, similar to those of Klehn, have been published (Arounaguiri et al., 1999). A porphyrin zinc complex was used for a 35 supramolecular "electro- and proto- photoswitch." This system is based on almost the same principles as Fabbrizzi's systems. One state is fluorescent, the other is not (Otsuki et al., 1999). Also, a "bicompartmental ligand" found its way into the literature. This system is quite similar to Shanzer's. The ligand possesses a hard and a soft cavity for Fe(III) and Fe(II). During the redox reaction an iron translocation takes place, similar to that described by Shanzer (Belle et al., 1998).

In the tris-([2-pyridyl]methyl)amine (TPA) family of ligands, a distinct twist of the pyridine rings with respect to the central axis of the molecules was observed. That is, the planes of the pyridine rings were always tilted with respect to the central axis of the structure. In crystals, both enantiomeric twisted conformations were present, and in solution, conformational enantiomerism was observed due to facile interconversion by C-C bond rotations. It was found that it was possible to bias the helical twist in TPA by incorporating a substituent in one of the $CH_2$ groups of the ligand, creating a chiral center (cf. FIG. 11, 1). This chiral center dictates the handedness of the propeller-like helicity of the pyridine moieties in compounds 1 and 3. The compounds were characterized in the solid state by X-ray crystallography and in solution by circular dichroism (CD) (Canary et al., 1995). Similar observations were made for all of the compounds 1–4 (Canary et al., 1998). There were remarkably large amplitudes for the CD spectra of the ligands, and it was found that the origin of the signal could be the quinoline rings in solution (Castagnetto et al., 1997). Complexes of several metal ions were studied; it was found that only metals that bind the ligand in a trigonal bipyramidal coordination geometry (ZnII, CuII) gave the propeller twist, and hence the large CD amplitudes. Metal ions forming octahedral complexes with 3 (FeII, CdII) gave a different ligand conformation (Cs), no twist, and low amplitude CD spectra.

The conformation-dependent chiroptical properties were applied to the development of a "smart" chemosensor for metal ions (Castagnetto et al., 1998). As noted above, only certain metal ions give enhanced CD signal amplitude upon binding to 3. It was found that ZnII and CdII give large enhancements in fluorescence intensity of the ligand, but that diamagnetic ions FeII and CuII do not. Thus, it was possible to show that 3 can give two signals, CD and fluorescence, and that these taken together result in the ability to discriminate between four possible metal ions, as shown in FIG. 12. To demonstrate a more practical and biorelevant application, it was shown that it was possible to generate calibration curves for detecting varying amounts of ZnII and CdII, and that a measurement of CD and fluorescence intensities of a single sample could give the concentrations of both species. Another possible application of this technology would be in the determination of ZnII levels in cells by microscopy enhanced with fluorescence-detected CE affording a low background compared with isotropic fluorescence measurements.

The present inventors also developed a method for determination of the absolute configuration of primary amines (Zahn et al., 1999 1). From the previous discussion, one can see that the sequence of the two Cotton effects in the CD spectra reveals the absolute configuration of the chiral atom in the tripod ligand. This correlation also holds true for ZnII complexes of a series of substituted quinoline compounds that were prepared with different substituents as shown in FIG. 13. Only compound 7 fails to give exciton-coupled CD spectra, probably due to the isopropyl group being so sterically encumbering that it distorts the complex. The ligands are prepared from primary amines; thus, derivatization of the primary amines by nucleophilic substitution of bromomethylquinoline (the method used in the synthesis) could be considered a method of absolute configuration determination of the amines. The present inventors have also now shown that the same approach can be used to determine the absolute configuration of α-amino acids and β-amino alcohols. Thus, reaction of an analyte with bromomethylquinoline on as small a scale as 3 mg, followed by addition of $Cu(ClO_4)_2$ and $NH_4SCN$, affords a CD spectrum that reveals the absolute configuration of the analyte.

The Cu(I) and Cu(II) complexes of the tripod ligands displayed varying degrees of "twistedness". (Chuang et al., 1995). This and the fact that the amplitude of the CD spectra of the chiral complexes was strongly dependent on the dihedral angle between the chromophores led the present inventors to investigate the development of a redox-write, CD-read molecular switch. The idea was that the twisting and untwisting of the trisquinoline ligand shown in FIG. 12 would give variable CD intensities. The compound was prepared and its chiroptical properties determined; the observed CD amplitude variation was even larger than predicted due to one quinoline arm decoordinating in the Cu(I) complex in the presence of SCN counterion. (Zahn et al., 1998). The data for this molecular switch were exceptionally gratifying in terms of the magnitude of the change and the reversibility of the spectra using solution techniques. Additionally, in collaboration with Prof. Gottarelli at the University of Bologna, the present inventors have found that the trisquinoline compounds can be added to nematic liquid crystalline phases to induce cholesteric phases.

SUMMARY OF THE INVENTION

It is an object of the present invention to overcome the aforementioned difficulties in the prior art.

It is another object of the present invention to produce electron-driven chirality switches.

A series of three dimensional complexes of an organic compound with a metal ion has been developed that exhibits unique conformational and spectroscopic properties upon changes in oxidation state of the metal ion. The metal (M in FIG. 14) is a redox-active metal ion (e.g., Cu(I)/Cu(II)) and may possess additional ligands bonded to it (e.g., solvent, counter ions) besides those depicted in the figure. The organic ligand has three "arms" that are linked together at a central atom ($A_1$ in FIG. 14), and each arm contains atoms that may also coordinate to the metal ion. At least two of the arms possess chromophoric properties ($C_1$ and $C_2$). At least one arm contains two different groups that may coordinate to the metal ion (e.g., via atoms $A_2$ or $A_3$). In one oxidation state, atom $A_2$ binds to the metal, while in the other oxidation state, the other atom $A_3$ binds to the metal. This change in coordination of the metal ion results in a rotation of the arm containing $A_2$ and $A_3$, which changes the orientation of group $R_5$. The result is an inversion of the orientation of the two chromophoric species with respect to one another.

The beauty of the present invention is the inversion of the orientation of two chromophores in three dimensions that results in a dramatic change in differential absorption of circularly polarized light. Thus, the present invention provides a system in which both the shape of the molecule as well as the optical properties can be changed.

Metal ions in different oxidation states may display quite different chemistry. In the present case, the polarizability of the metal increases upon increasing the number of electrons in the valence shell of the metal ion. Increasing the polarizability of a metal ion increases its tendency to bond with softer atoms. For example, reduction of Cu(II) to Cu(I) increases the relative tendency of the copper atom to prefer bonding with sulfur vs. oxygen, with Cu(II) being "oxophilic" and Cu(I) being "sulfophilic".

Thus, in the present invention, a tripod ligand is presented in which one arm presents a choice to the metal ion. The atoms $A_2$ and $A_3$ in FIG. 14 differ in character, such that one or the other of the two atoms is preferred by the metal ion, depending upon its oxidation state. Changing the oxidation state by chemical or electrical means results in a change in which atom is bonded preferentially. Thus, upon an oxidation or reduction event, the arm containing $A_2$ and $A_3$ rotates about pivot atom P so that the preferred atom may come into contact with the metal ion.

In FIG. 14,

A=atom that can coordinate to a metal ion, e.g., N, O, S

C=chromophore capable of absorbing light that also contains an atom that may coordinate to a metal ion z=pivot atom (chiral atom, e.g., C)

$R_1$–$R_4$=linker groups $R_5$–$R_7$=terminal groups

M=metal ion

The rotation about the pivot atom changes the orientation of the plane defined by $A_2$, M, and $A_3$ with respect to the central axis of the molecule, defined by the line containing M and $A_1$. The same change in stereochemistry can be seen by the change in the orientation of $R_5$: In FIG. 14, $R_5$ is behind the plane of the drawing in the oxidized structure (left); it is in front of the plane in the reduced structure (right). This results in a re-orientation of the two chromophores, $C_1$ and $C_2$. In the structure on the right in FIG. 14, the chromophores are arranged in an orientation which would be described conventionally as "negative chirality", while on the right the orientation is in a positive chiral sense. The interconversion comes about as a result of changes in the steric environment around Z (and attached atoms), $R_2$, and $R_3$. The overall result is that the pivot of the arm causes chromophores $C_1$ and $C_2$ to change orientation. If we consider the orientation of the chromophores as a center of axial chirality (e.g., not with respect to a point as in atom P but a plane), then this chiral center is inverted.

Since the chromophores are often large compared to the pivot arm, the change in overall shape of the molecule is magnified. For example, if the planes of the chromophores and the plane defined by $A_2$, M, and $A_3$ are viewed as a propeller, the direction of the propeller is inverted upon changing the oxidation state of the metal ion. Recently, collaboration with scientists at the University of Bologna has provided data that this shape change can be useful. It has been shown that these compounds (both the on/off and +/– switch compounds) can be used to dope nematic liquid crystalline materials to induce cholesteric phases. The chiral cholesteric phases for materials doped with Cu(I) vs Cu(II) complexes of the same ligand gave opposite helical twisting powers, just as would be expected as the overall twist of the molecule is inverted.

The presence of two chromophores in the molecule and their close proximity to one another results in a unique spectroscopic signature. This arrangement gives rise to an exciton-coupled circular dichroism signal (ECCD), a result of quantum mechanical coupling of the two electronic transitions in the chromophores (Castagnetto et al., 1997). This phenomenon has been studied widely and shown to give signals that depend on the absolute sense of chiral orientation of the chromophores. That is, chromophores with opposite chirality give mirror image spectra. This is observed in the present system, as shown for the compounds that have been studied.

The complexes of the present invention can be used in, "molecular electronics." For example, the molecular switch can be used as a redox-write, chiroptical read data storage device. In this application, the switching between + and – states is analogous to the 1 and 0 binary logic states used in data storage. The advantage of the new technology is that the new molecular switch can be reduced to much higher density of data storage than the presently used macroscopic magnetic media. Additionally, the system may be used as non-volatile memory since power does not need to be applied constantly to maintain the data. It should also be noted that ample precedence exists for photo-oxidation/photo-reduction of coordination complexes, such that the invention is adaptable to writing with light as well as reading.

Another application of the present invention is in the area of optical display devices. Present liquid crystal display technology makes use of cross-polarizers with liquid crystalline materials that are modulated by an electric field. The molecules of the present invention can be used to replace the cholesteric liquid crystalline materials since they exert very strong optical polarization, which may be modulated with electric current. An advantage to the system of the present invention is that the display would not require constant supply of electricity, but would retain its polarizing power, and thus its image, when the power is turned off. Such a strategy may ultimately require less power in order to operate than currently used displays.

DETAILED DESCRIPTION OF THE INVENTION

Figure 1:
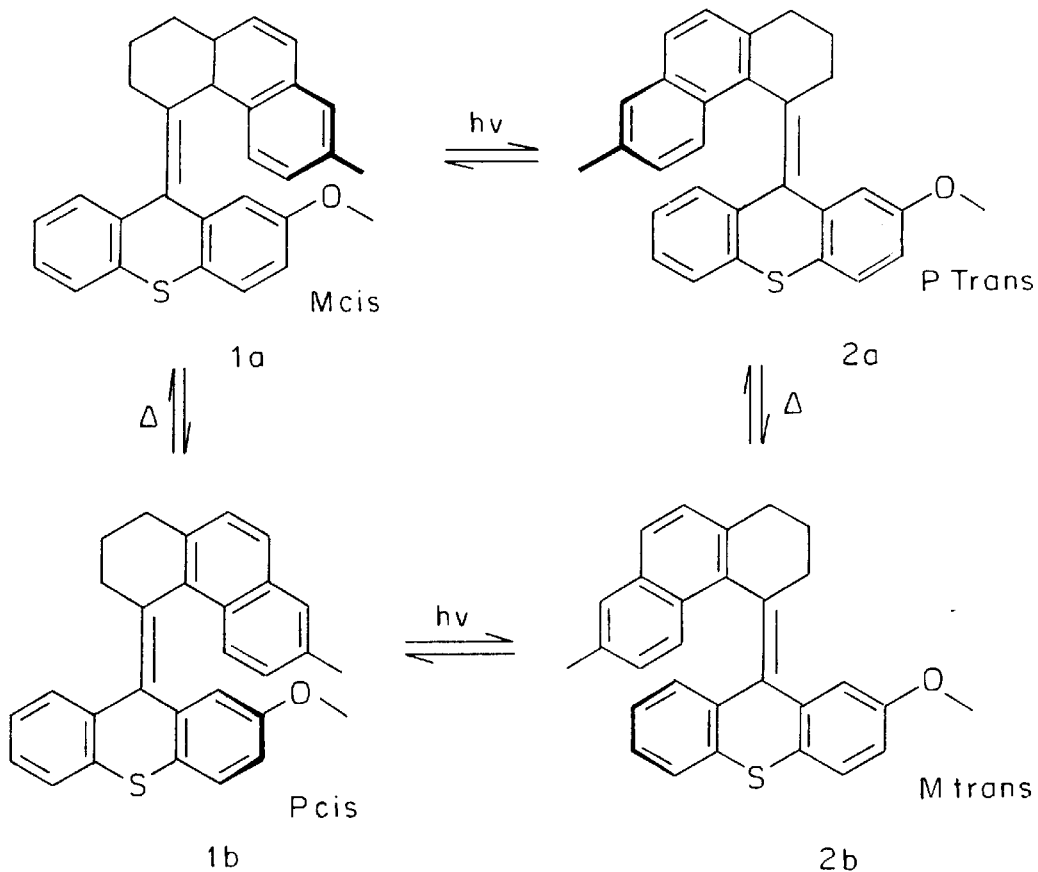
FIG. 1 shows stable enantiomers of thioxanthenes.
Figure 2:
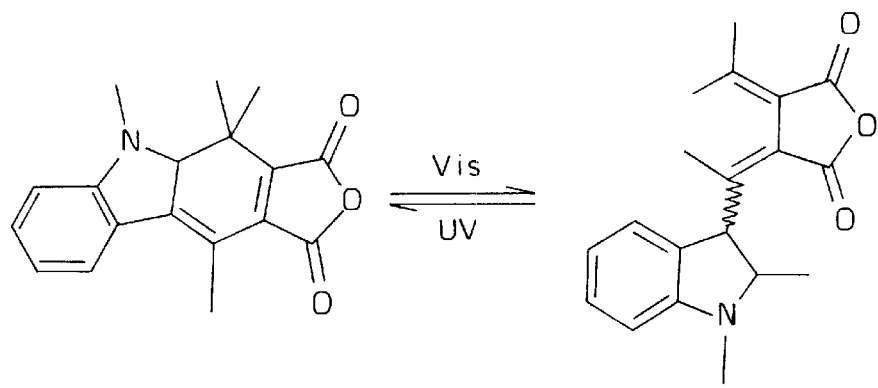
FIG. 2 shows an optical switch which is sensitive to visible/uv light.
Figure 3:
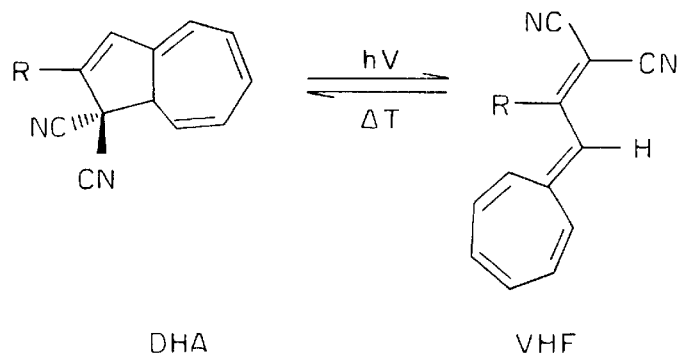
FIG. 3 illustrates a dihydroazulene/vinylheptafulvene photochroism system.
Figure 4:
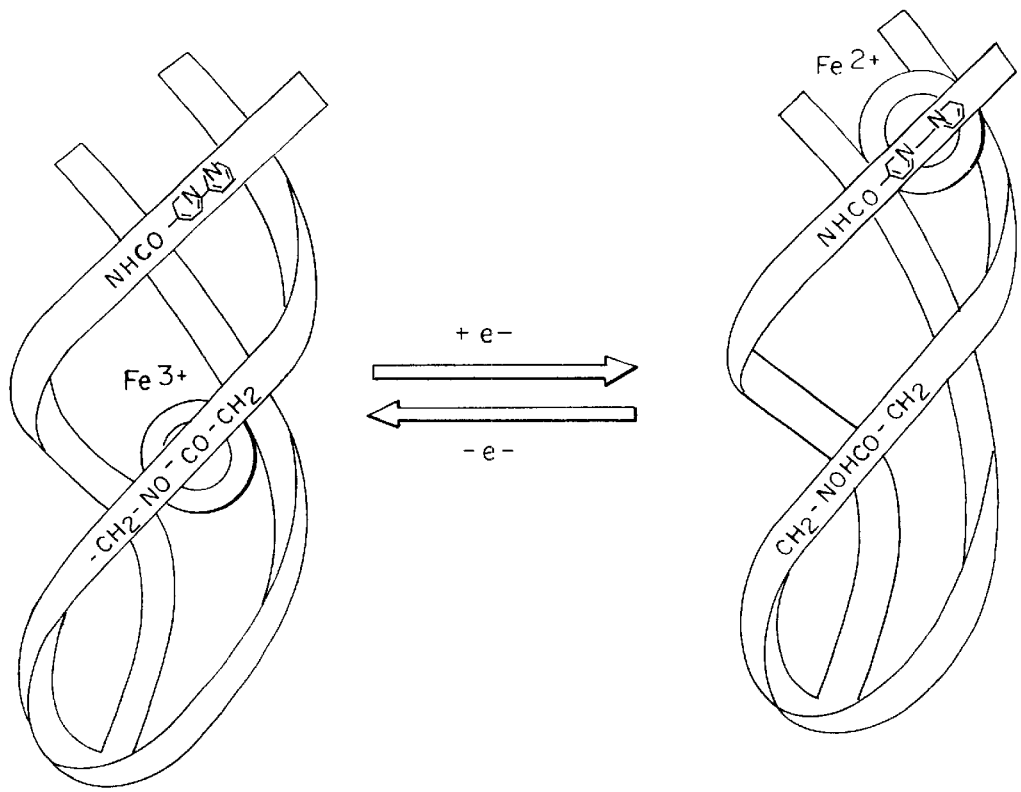
FIG. 4 illustrates redox switches for Fe(II) and Fe(III).
Figure 5:
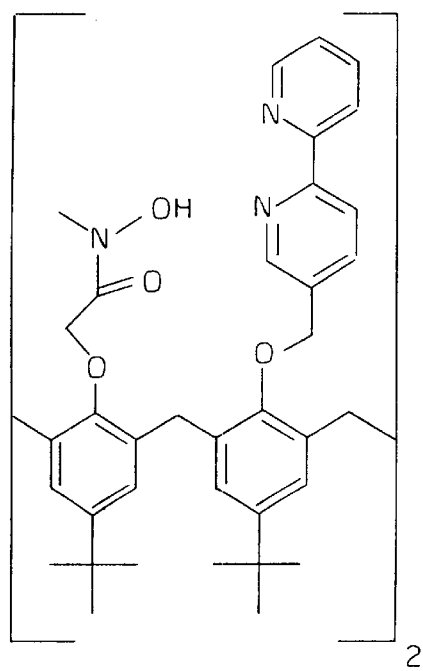
FIG. 5 illustrates another version of a redox switch using one set of hard and one set of soft ligating groups.
Figure 6:
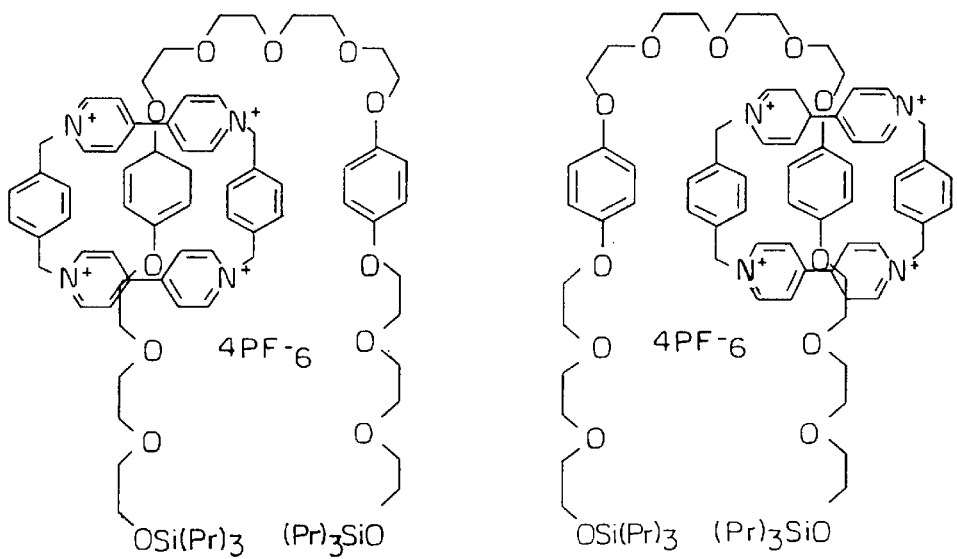
FIG. 6 shows [2]-rotaxane operating as a molecular shuttle wherein a teracationic bis-pyridium cyclophane moves back and forth between two binding sites.
Figure 7:
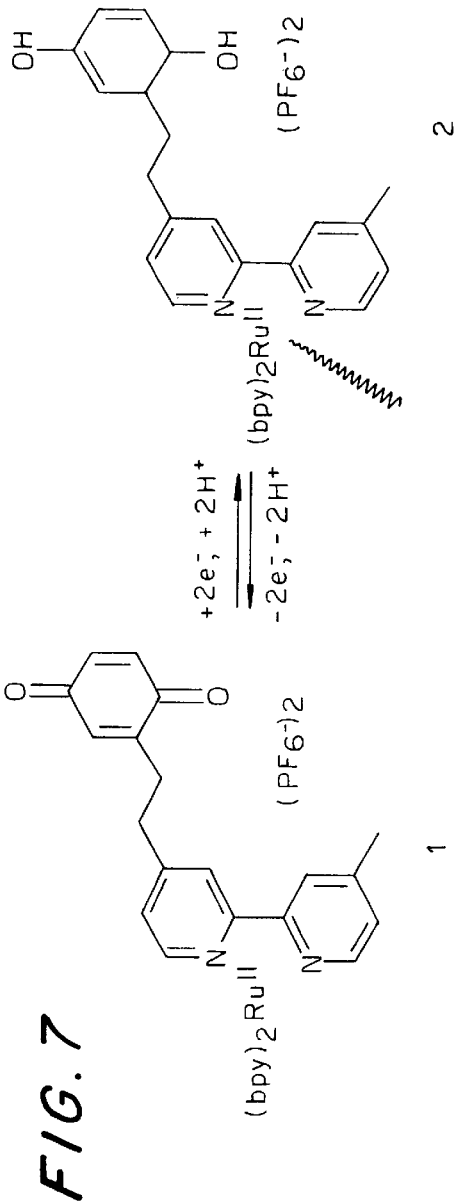
FIG. 7 illustrates a molecular switching system that effects the redox on/off switching of luminescence and combines an electroactive component with a light-emitting center.
Figure 8:
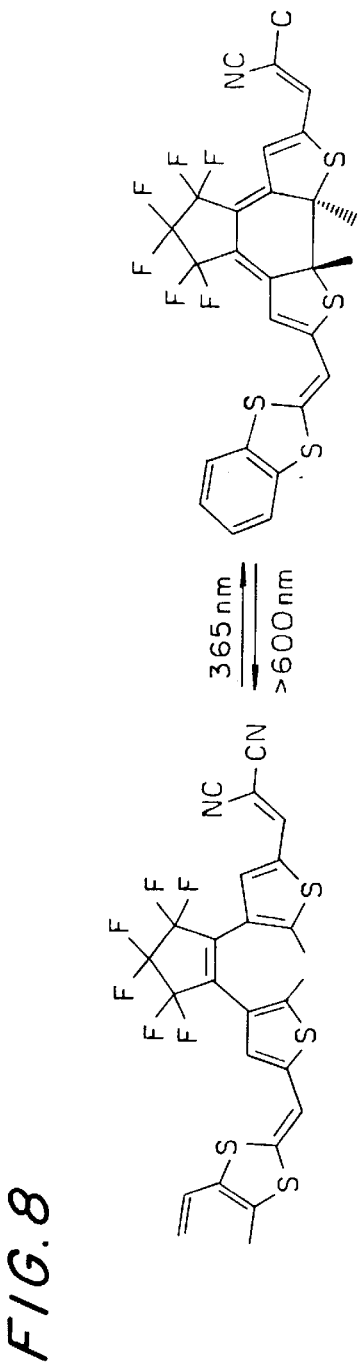
FIG. 8 shows electrically triggered swinging of a [2]-catenate.
Figure 9:
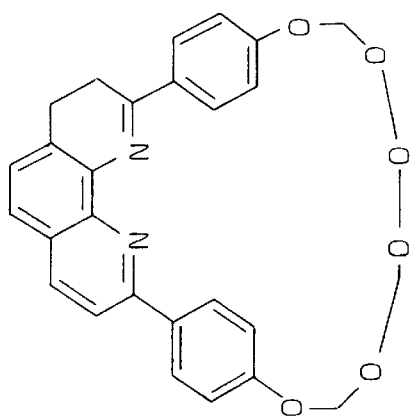
FIG. 9 shows interconversion between two forms of a complex.
Figure 9:
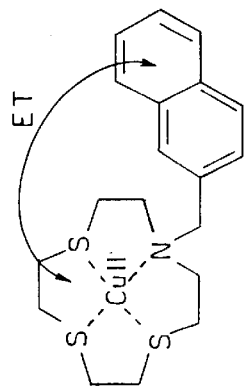
Figure 9:
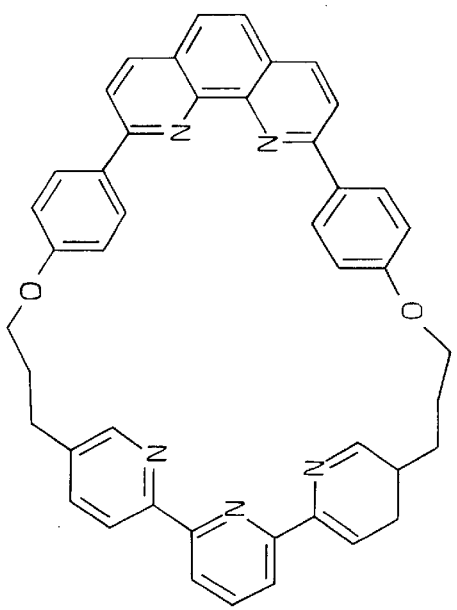
Figure 10:
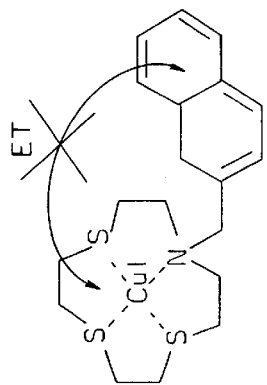
FIG. 10 shows a redox-active metal positioned within a tetradentate ligand tethered to a fluorophore.
Figure 11:
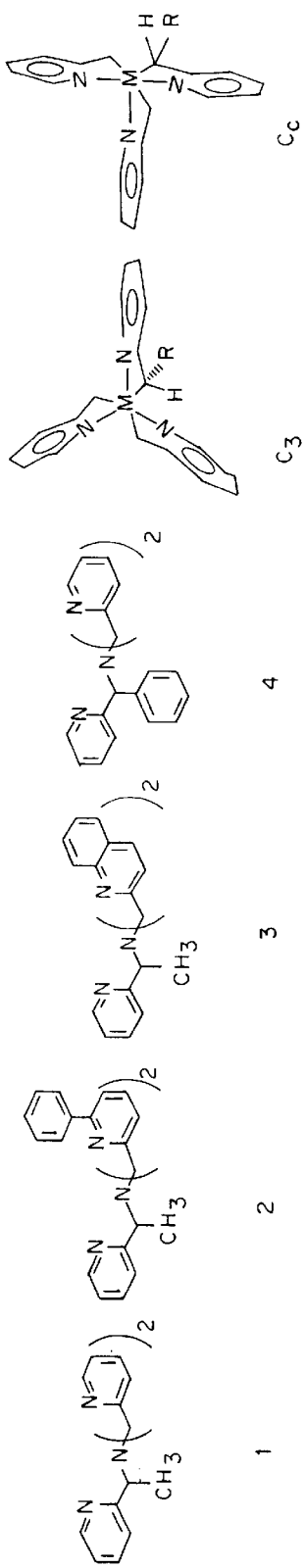
FIG. 11 shows tris [(2-pyridyl)-methyl] amine types of ligands.
Figure 11:
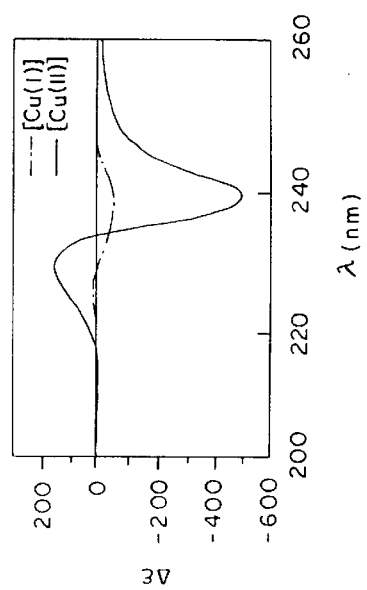
Figure 11:
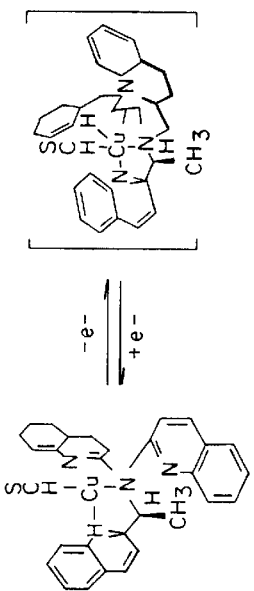
Figure 11:
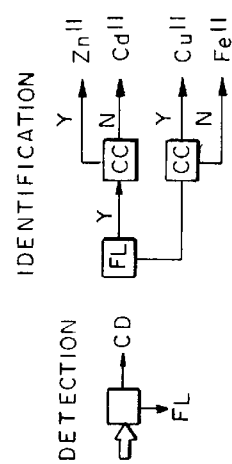
Figure 12A:
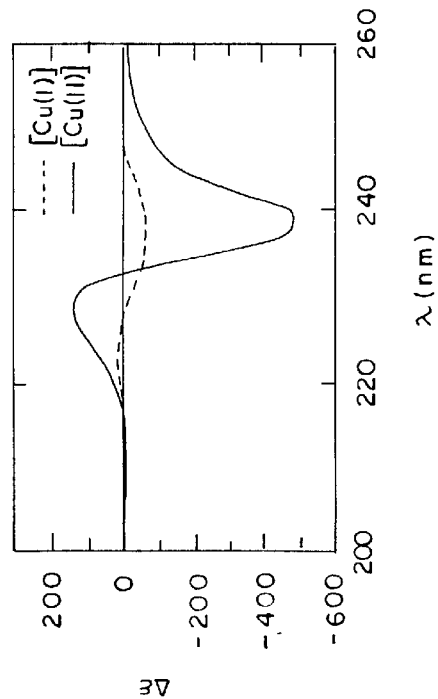
FIG. 12a illustrates discrimination between four metal ions using fluorescence and CD.
Figure 12A:
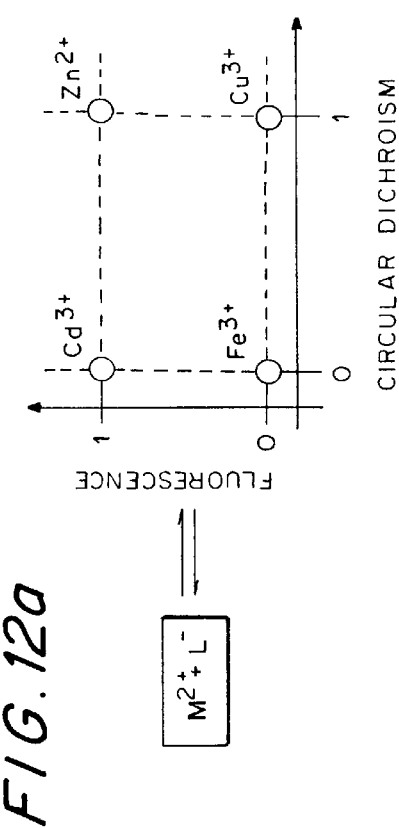
Figure 12B:
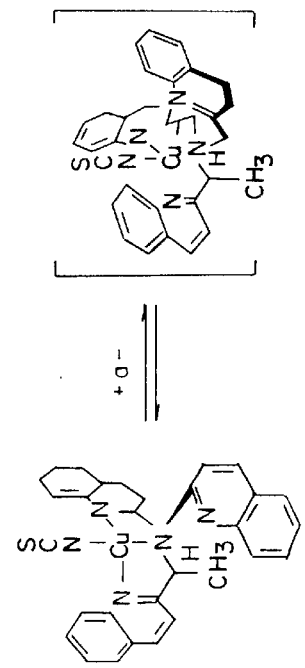
FIG. 12b illustrates redox-switches for $Cu^+$ AND $Cu^{2+}$.
Figure 13:
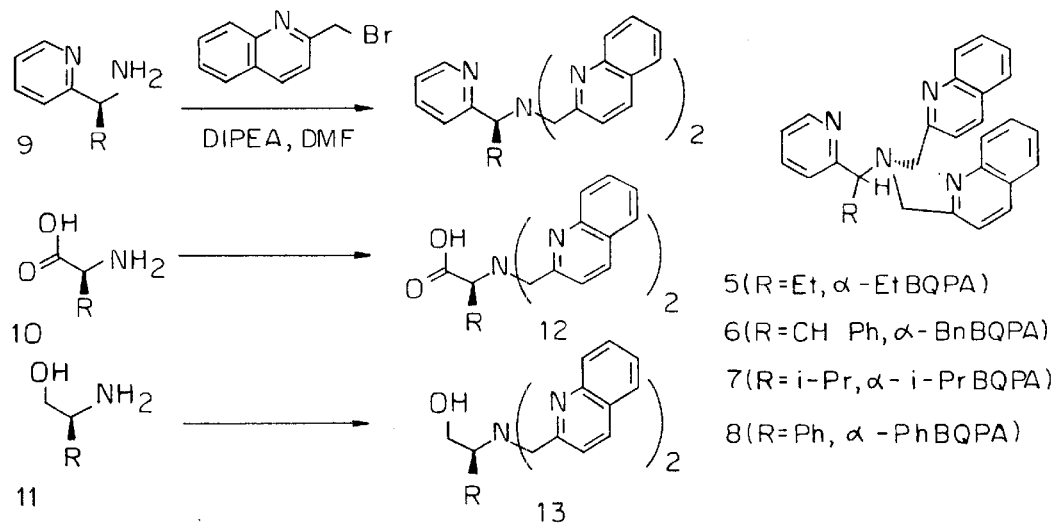
FIG. 13 shows a series of substituted quinoline compounds prepared with different substituents.
Figure 14:
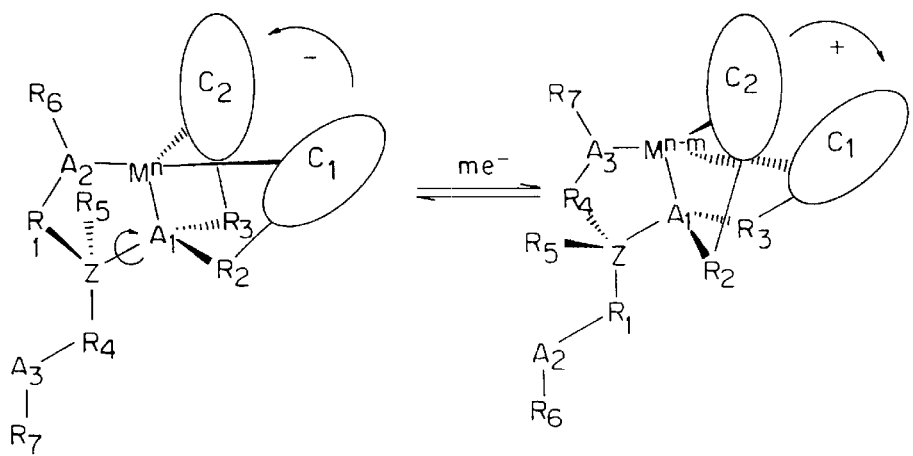
FIG. 14 shows a tripod ligand in which one arm presents a choice to the metal ion.

In the formula shown in FIG. 14, A is an atom that can coordinate to a metal ion such as nitrogen, oxygen, or sulfur;

$C_1$ and $C_2$ are the same or different chromophores capable of absorbing light that also contain an atom that may coordinate to a metal ion;

Z is a pivot atom, or chiral atom, e.g., carbon;

$R_1$–$R_4$ are linker groups, and may be —$(CH_2)_n$—, —O—, —S—, —$NR_8$—, carbonyl, carboxyl, wherein n can be an integer of from 1 to 4

$R_8$ is straight-chain or branched alkyl having from 1 to 8 carbon atoms.

$R_5$–$R_7$ are terminal groups which can be hydrogen, $C_1$–$C_8$ branched or straight chain alkyl groups, $C_6$–$C_{14}$ substituted or unsubstituted aromatic groups and heteroaromatic groups having from one to three hetero atoms. The hetero atoms can be nitrogen, sulfur, or oxygen.

M is a metal ion which can exist in at least two oxidation states.

The basic switching mechanisms of the present invention can be used with any metal ion that exists in two oxidation states. When using circular dichroism spectroscopy as a spectroscopic reporter, the preferred metal ions are those with trigonal bipyramidal coordination sphere, such as copper and zinc.

The chromophores, which may be the same or different, can be any chromophore that also binds to a metal. Examples of such chromophores are substituted and unsubstituted pyridines, quinolines, imidazoles, pyrazoles, pyrazines, pyridiazines, benzimidazoles, phenanthrolines, and related heterocyclic compounds having one or more rings, which may be fused, that are chromophores that also bind to a metal ion. The substituents can be aliphatic, aromatic, or alkyl aromatic having from 1 to 16 carbon atoms, nitro, cyano, $C_1$–$C_8$ alkoxy, $C_1$–$C_{16}$ aryloxy, $C_1$–$C_8$ alkylamino, $C_1$–$C_{16}$ arylamino, azo, halo, sulfonyl, phosphoryl, $C_1$–$C_8$ alkylthio, $C_1$–$C_{16}$ arylthio, or any other substituent that does not affect the metal ion binding and the chromophoric properties of the molecule.

The present invention is thus directed to coordination compounds which can be used to exhibit conformational and spectroscopic properties depending upon the oxidation state of the metal ion complexed within. The coordination compounds of the present invention include any chromophore that can bind to a metal, a coordination metal which can exist in two valence states, and a chiral unit that can rotate so as to obtain distinguishing physical properties of the coordination compounds.

By inverting the orientation of the two chromophores in three dimensions in the coordination compounds of the present invention, one can produce a change in the differential absorption of circularly polarized light or rotation of plane polarized light. This changes both the shape of the molecules and the optical properties of the molecules. These compounds can be used for redox write, chiroptical read storage devices, as well as in place of liquid crystal materials in display devices.

The chirality may be inverted for the oxidation states, such that the oxidized compound gives "+" chirality and the reduced compound gives "−" chirality.

Figure 15:
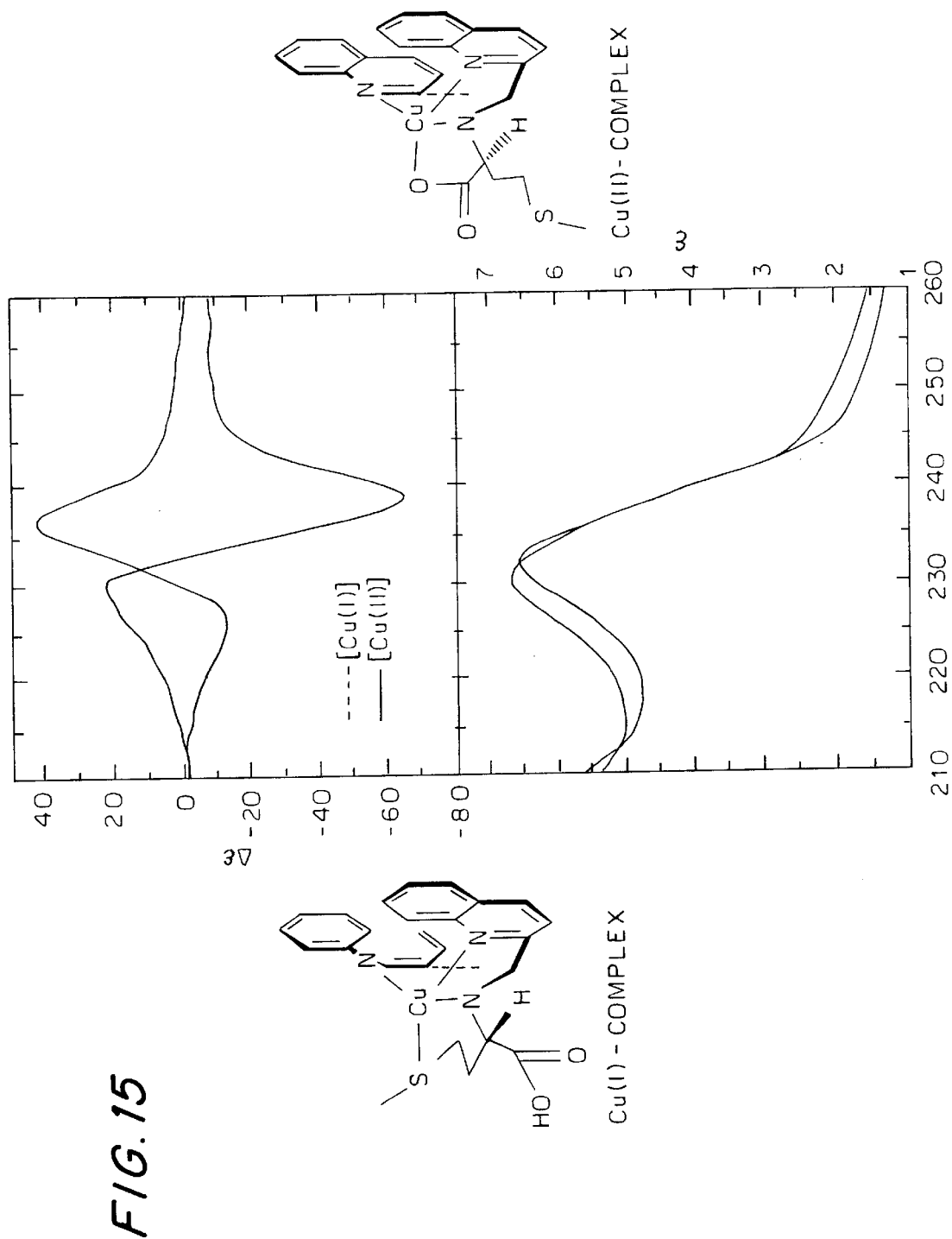
FIG. 15 shows the shift between Cu(I) and Cu(II) in a complex according to the present invention.

An illustration of such a compound is shown in FIG. 15, in which Cu(I) is complexed with a sulfur atom and Cu(II) is complexed by an oxygen atom. The Δε for each of Cu(I) and Cu(II) are shown in the graph in the center of FIG. 15.

The present invention is similar to the "on/off" molecular switches as described by (Zahn et al., 1998 and Zahn et al., 1998) in that molecular motion in a coordination complex results in a change in signal in the circular dichroism spectrum. However, the nature of the motion is different, and the new switch does not simply turn the signal on and off but causes an interconversion between mirror images (i.e., "+/- switch").

The following examples illustrate compounds which can be used for electron-driven chirality switches. These examples are solely for illustration, and in no way are intended to limit the invention.

Preparation of Free Ligand

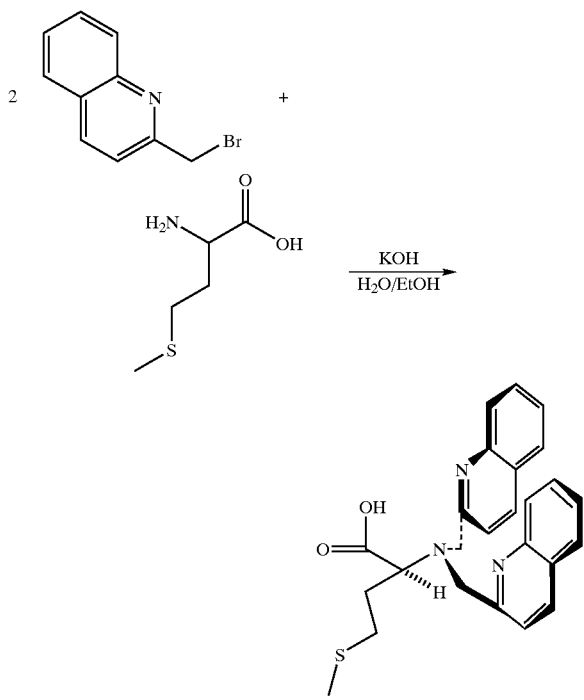

To 24 g (0.016 mol) of commercially available L-methionine in 9 mL of water was added 2.7 g KOH (0.048 mol) and 4 ml of ethanol. The solution was heated to reflux and 7.1 g 2-bromomethyl-quinoline (0.032 mol) dissolved in 20 mL of ethanol was added over 10 minutes. The resulting solution was refluxed for 60 minutes, cooled and evaporated to one half the original volume. The solution was extracted with methylene chloride. The methylene chloride layer was collected, dried over anhydrous potassium carbonate and evaporated to dryness. Column chromatography (NP-Silica, Ethyl acetate/Hexanes:3/1) yielded 2 g (29%) of the elementally pure product.

Preparation of Cu(I) Complex

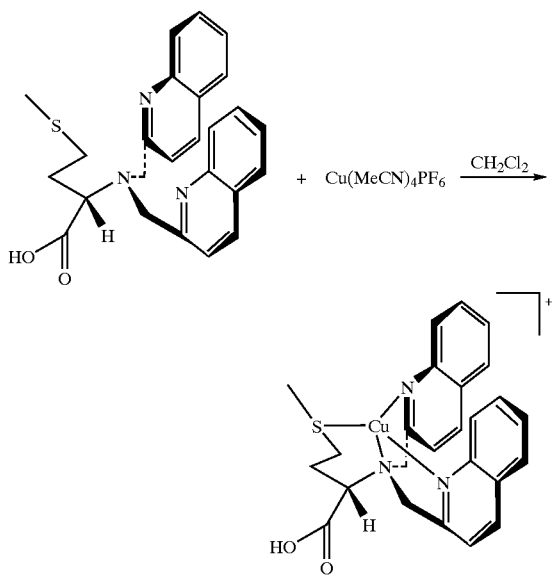

Deoxygenated, HCl-free methylene chloride (10 mL) was added to mixture of 100 mg of the solid ligand (0.23 mmol) and 85 mg of Cu(MeCN)$_4$PF$_6$ (0.22 mmol) under nitrogen. The solution was stirred for 5 minutes and 20 mL diethylether were added to crystallize the copper complex. The precipitate was collected, washed with diethylether and dried in vacuo to yield 122 mg (82%) of the desired compound elementally pure.

Preparation of Cu(II) Complex

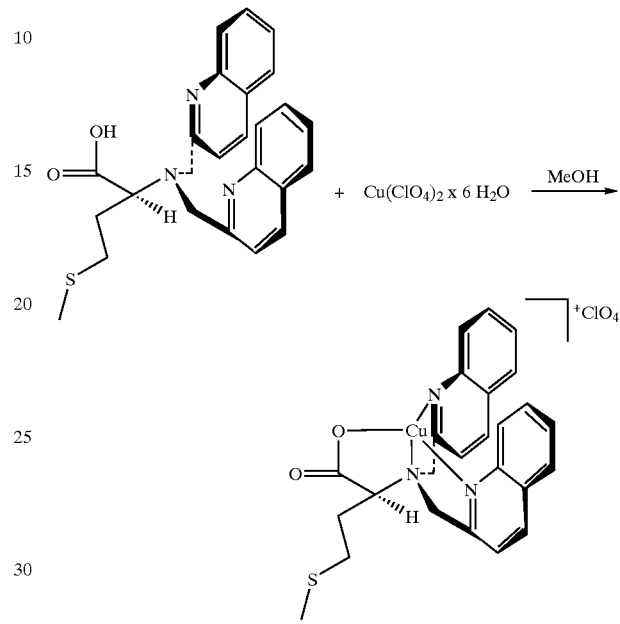

A mixture consisting of 180 mg of the solid ligand (0.417 mmol) and 162 mg Of Cu(ClO$_4$)$_2$×6 H$_2$O (0.418 mmol) was dissolved in 30 mL methanol. Upon stirring for one hour a precipitate formed, which was collected washed with methanol and dried in vacuo to yield 140 mg of the elementally pure copper complex.

Preparation of Free Ligand

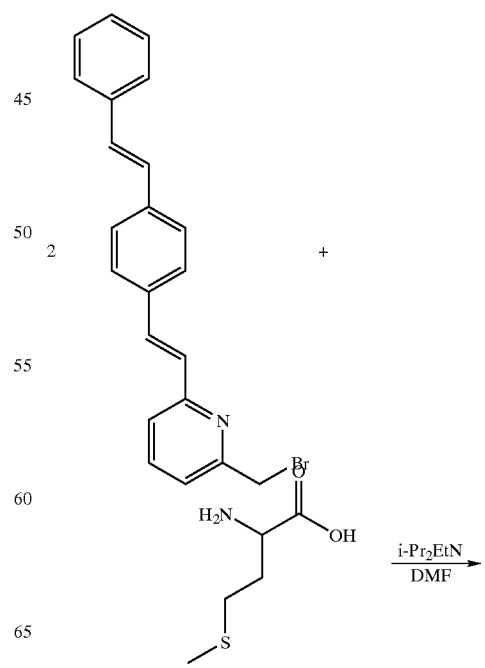

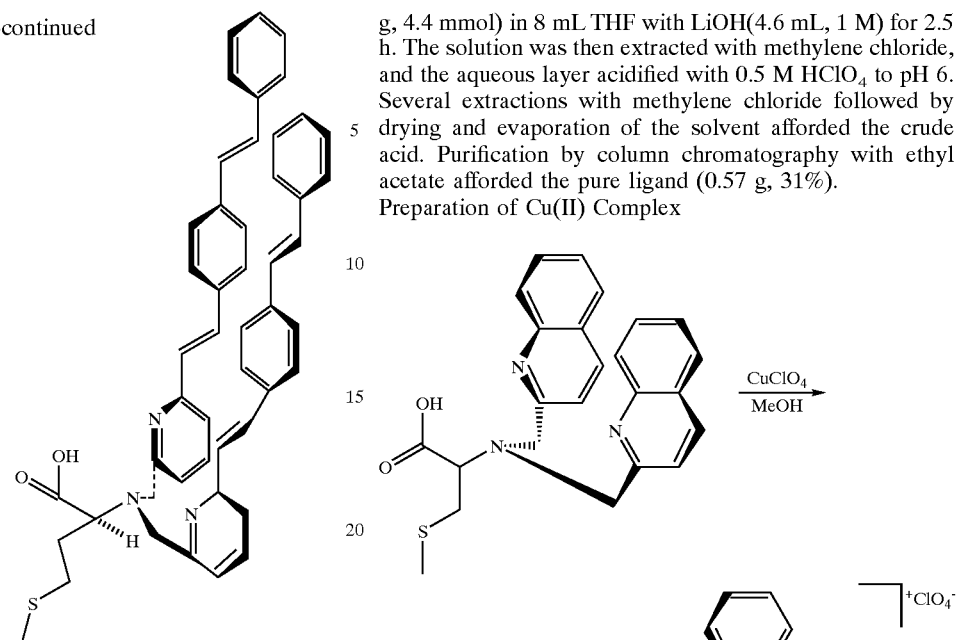

To 13 mL of dimethylformamide at 80° C. were added 500 mg of the bromide and 0.45 mL of degassed i-Pr$_2$EtN. To this solution were added 100 mg of L-methionine dissolved in 3 mL of a 2:1 water:DMF mixture containing 10 mg sodium bicarbonate dropwise. The reaction was stirred for 5 hours at 80° C., cooled and evaporated to dryness. The remaining solid was taken up in a methylene chloride/sodium hydroxide (1 M) mixture (1:1). The organic layer was collected, dried over anhydrous potassium carbonate and chromatographed to yield 200 mg of the desired ligand.

Preparation of Ligand

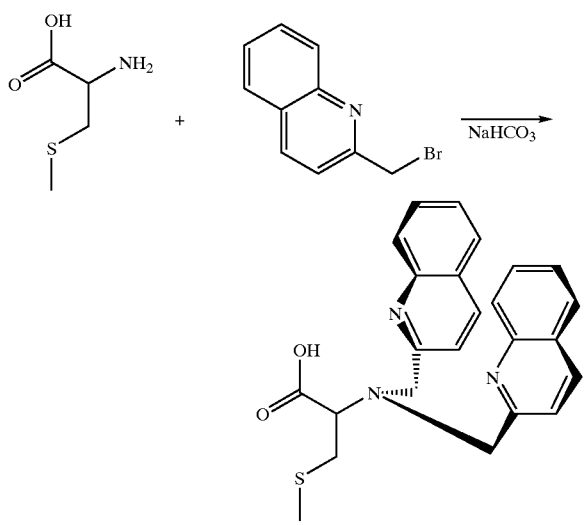

The ligand N,N-bis[(2-quinolyl)methyl]-(S)-methly-L-cysteine was prepared from the dropwise addition of (S)-methyl-L-cysteine methylester hydrochloride (2.0 g, 10.8 mmol) in 10 mL DMF to a stirring solution of 2-bromomethylquinoline (4.8 g, 21.6 mmol) and sodium bicarbonate (4.1 g, 49 mmol) in 40 mL. The mixture was allowed to react for 4 h at 80° C. Evaporation of the solvent followed by column chromatography with 3:1 hexanes: ethyl acetate (Rf 0.3) afforded the ester of the ligand (1.7 g, 82%). Saponification was achieved by stirring the ester (1.9 g, 4.4 mmol) in 8 mL THF with LiOH(4.6 mL, 1 M) for 2.5 h. The solution was then extracted with methylene chloride, and the aqueous layer acidified with 0.5 M HClO$_4$ to pH 6. Several extractions with methylene chloride followed by drying and evaporation of the solvent afforded the crude acid. Purification by column chromatography with ethyl acetate afforded the pure ligand (0.57 g, 31%).

Preparation of Cu(II) Complex

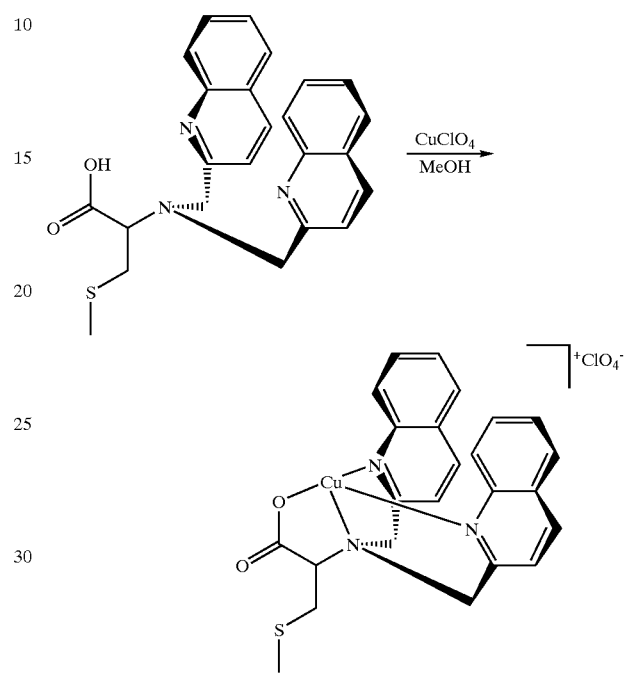

Complexation of the pure ligand (0.097 g, 232 mmol) with equimolar amount of CuClO$_4$·H$_2$O in MeOH afforded blue crystals which were collected by vacuum filtration and washed with ether (0.129 g, 78%).

Preparation of Ligand

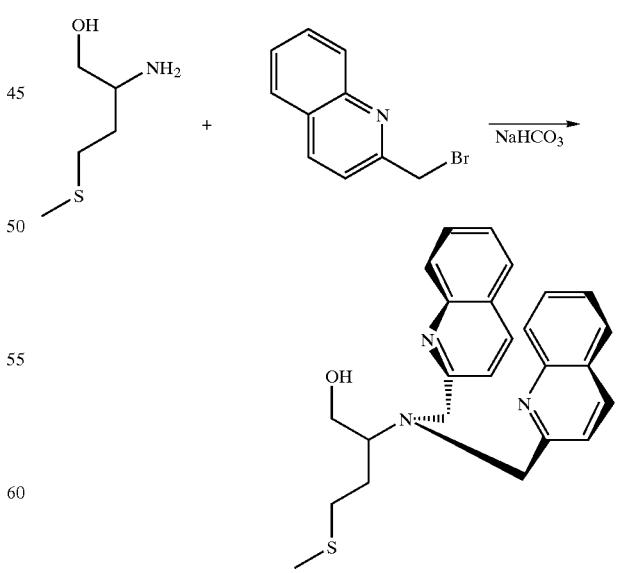

3.27 grams of 2-bromomethylquinoline and 2.8 g of sodium bicarbonate were stirred in 15 ml of DMF. The mixture was heated to a constant temperature between 60–70 degrees with magnetic stirring. 1.0 g of L-methioninol dissolved in 5 ml of DMF was added drop wise to the reagent flask. The resulting mixture was heated between 60–70 degrees Celsius. After cooling down to room temperature, sodium bicarbonate was filtered and the DMF was evaporated and vacuum dried overnight Purification with silica column chromatography (Rf 0.15) yielded 1.17 g (38.11%) of (L)-N,N-bis(2-quinaldyl)methionol.

Preparation of Cu(II) Complex

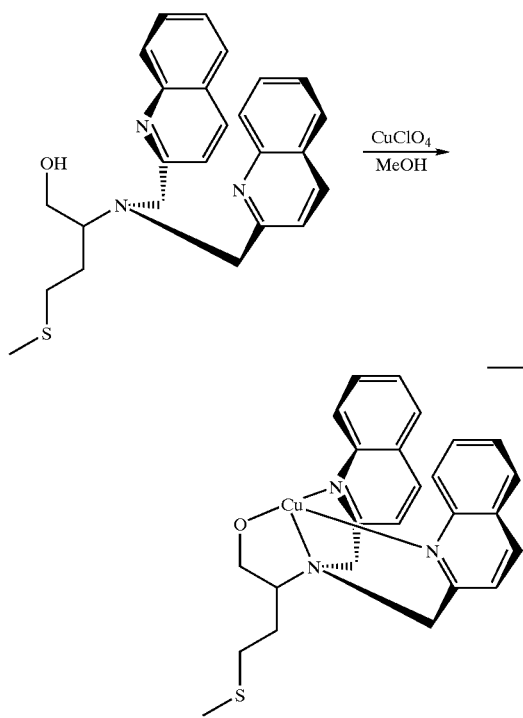

100 mg of N,N-bis(2-quinaldyl)methioninol was dissolved in 1 ml of methanol. 0.99 g of $CU(II)ClO_4·6H_2O$ in 1–2 ml of methanol was slowly added to the above solution. A green-blue precipitate formed immediately. The precipitate was filtered and washed with ethyl ether. Vacuum drying overnight yielded the complex (41.58%).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehend within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . " or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment to embodiments disclosed in the specification above, i.e., other means or steps for carrying out the same function can be used; and it is intended that such expressions be given their broadest interpretation.

REFERENCES

Arounaguiri et al., Inorg. Chem., 38:842–843 (1999).
Belle et al., New. J. Chem., 22:1399–1402 (1998).
Burk et al., Angew. Chem. Int. Ed. Engl., 29:1462 (1990).
Canary et al., "Conformationally Driven, Propeller-Like Chirality in Labile Coordination Complexes," J. Am. Chem. Soc., 117:8484–8485 (1995).
Canary et al., "Solid State and Solution Characterization of Chiral, Conformationally Mobile Tripodal Ligands," Inorg. Chem., 37:6255–62 (1998).
Castagnetto et al., "Absolute Configurational Assignment of Self-Organizing symmetric Tripodal Ligand-Metal Complexes," Chirality, 9:616–622 (1997).
Castagnetto et al., "A Chiroptically Enhanced Fluorescent Chemosensor," J. Chem. Soc., Chem. Commun., 203:4 (1998).
Canavet et al., Angew. Chem. Int. Ed. Engl., 35:2657–2659 (1996).
Chuang et al., "Synthesis, Cyclic Voltammetry and X-Ray Crystal Structures of Copper(I) and Copper(II) Complexes of Tris(6-phenyl-2-pyridylmethyl)amine (TPPA)," Inorg. Chem., 34:2562–2568 (1995).
Eliel et al., "Stereochemistry of Organic Compounds" John Wiley & Sons, Inc.; New York (1994).
Fabbrizzi et al., Chem. Soc. Rev. 197–202 (1995).
Feringa et al. J. Am. Chem. Soc., 113:5468–5470 (1991).
Giltam et al., Chem. Eur. J., 1:285–293 (1995)
Goulle et al., J. Chem. Soc., Chem. Commun., 1034–1036 (1993).
Huck et al., Science, 273:1686–1688 (1996).
Janicki et al., J. Am. Chem. Soc., 117:8524–8527 (1995).
Lehn, "Supramolecular Chemistry—Concepts and Perspectives, VCH", Weinheim (1995).
Livoreil et al., J. Am. Chem. Soc., 116:9399–9400 (1994).
Otsuki et al., Chemistry Letters, 269–270 (1999).
Spreitzer et al., Chem. Eur. J., 2:1150–1158 (1996).
Stoddart et al., J. Am. Chem. Soc., 114:193 (1992).
Zahn et al., Science, 288:1404–1407.
Zahn et al., "Absolute Configurations of N,N-Dialkyl Alpha Amino Acids and Beta Amino Alcohols from Exciton Coupled Circular Dichroism Spectra of Cu(II) Complexes," Org. Lett. 1999, 1.
Zahn et al., "Redox-Switched Exciton-Coupled Circular Dichroism: A Novel Strategy for Binary Molecular Switching," Angew. Chem., Int. Ed. Eng., 37:305–7 (1998).
Zahn et al., "Redoxschaltbarer, excitonengekoppelter Circulardichroismus: eine neue Strategie fur die Entwicklung molekularer Schalter," Angew. Chem., 110:321–3 (1998).
Zelikovich et al., Nature, 374:790–792 (1995).

What is claimed is:

1. A coordination complex comprising:
    (a) a metal ion that exists in two different oxidation states:
    (b) a chiral unit that contains two atoms that can ligate to the metal ion, and wherein a different atom ligates to the metal ion in each oxidation state of the metal ion; and
    (c) an organic ligand containing three arms linked together at said metal ion wherein each arm contains atoms that are capable of coordinating to the metal ion, and at least two of the arms possess chromophoric properties.

2. The coordination complex according to claim 1 wherein at least one arm contains a first group that coordinates to the metal ion in a first oxidation state and a second group that coordinates to the metal ion in a second oxidation state.

3. A coordination complex having the formula:

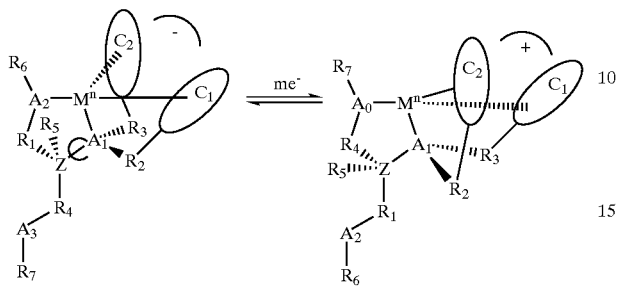

wherein
A is an atom that coordinates to a metal ion;
$C_1$ and $C_2$ are the same or different chromophores capable of absorbing light that also contain an atom that is capable of coordinating to a metal ion, or $C_1$ and $C_2$ are chromophores appended to groups containing an atom that is capable of coordinating to a metal ion;
Z is a chiral atom;
$R_1$–$R_4$ are linker groups selected from the group consisting of —$(CH_2)_n$—, —O—, —S—, —$NR_8$—, carbonyl, carboxyl;
n is an integer of from 1 to 4
$R_8$ is straight-chain or branched alkyl having from 1 to 8 carbon atoms.
$R_5$–$R_7$ are terminal groups selected from the group consisting of hydrogen, $C_1$–$C_8$ branched or straight chain alkyl groups, $C_6$–$C_{14}$ substituted or unsubstituted aromatic groups and heteroaromatic groups having from one to three hetero atoms wherein the hetero atoms are selected from the group consisting of nitrogen, sulfur, and oxygen; and
M is a metal ion that can exist in more than one oxidation state.

4. The coordination complex according to claim 3 wherein A is selected from the group consisting of N, O, and S.

5. The coordination complex according to claim 3 wherein either one of $C_1$ or $C_2$ is selected from the group consisting of substituted pyridines, unsubstituted pyridines, quinolines, substituted quinolines, imidazoles, substituted imidazoles, pyrazoles, substituted pyrazoles, pyrazines, substituted pyrazines, pyridazines, substituted pyridazines, benzimidazoles, substituted benzimidazoles, phenanthrolines, substituted phenanthrolines, chromophoric heterocyclic compounds having at least two rings which are optionally fused;
wherein the substituents are selected from the group consisting of $C_1$–$C_8$ aliphatic, $C_6$–$C_{16}$ aromatic, $C_7$–$C_6$ alkyl aromatic, nitro, cyano, $C_1$–$C_8$ alkoxy, $C_1$–$C_{16}$ aryloxy, $C_1$–$C_8$ alkylamino, $C_1$–$C_{16}$ arylamino, azo, halo, sulfonyl, phosphoryl, $C_1$–$C_8$ alkylthio, and $C_1$–$C_{16}$ arylthio.

6. The coordination complex according to claim 3 wherein $R_1$–$R_4$ are selected from the group consisting of (—$CH_2$—)$_n$—O—, —S——NH—

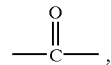

and

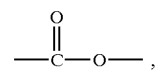

and n is an integer of from one to eight.

7. The coordination complex according to claim 3 wherein $R_5$–$R_7$ are selected from the groups consisting of hydrogen and methyl.

8. The coordination complex according to claim 3 wherein the metal ion binds the ligand in trigional bipyramidyl coordination geometry.

9. The coordination complex according to claim 8 wherein the metal ion is Cu(II) or Zn(II).

10. A coordination complex of the formula:

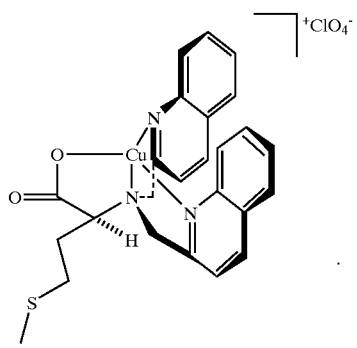

11. A coordination complex comprising:
a. a metal ion that exists in two different oxidation states;
b. an organic ligand contains three arms linked together at the metal ion wherein each arm contains atoms that can coordinate to the metal ion;
c. wherein at least one arm contains two different groups that can coordinate to the metal ion, wherein when the metal is in a first oxidation state one of the two different groups coordinates to the metal ion, and when the metal is in a second oxidation state the other of the two different groups coordinates to the metal ion.

* * * * *